United States Patent [19]
Amendola et al.

[11] Patent Number: 5,799,673
[45] Date of Patent: Sep. 1, 1998

[54] DENTAL FLOSS WITH FINGER LOOPS AND DISPENSER

[76] Inventors: Wayne J. Amendola; Elizabeth Amendola, both of 1395 Riverside Cir., Wellington, Fla. 33414; David L. Volk, 301 Oakwood Ct., Clairton, Pa. 15025

[21] Appl. No.: 4,724

[22] Filed: Jan. 3, 1998

Related U.S. Application Data

[63] Continuation of Ser. No. 784,091, Jan. 15, 1997, abandoned.
[51] Int. Cl.⁶ .................................................. A61C 15/00
[52] U.S. Cl. .................................... 132/321; 206/820
[58] Field of Search .............................. 132/321, 323, 132/324, 325; 206/820

[56] References Cited

U.S. PATENT DOCUMENTS

| | | | |
|---|---|---|---|
| 3,485,349 | 12/1969 | Chaney, Jr. ...................... | 206/820 |
| 3,802,445 | 4/1974 | Wesley ........................... | 132/321 |
| 4,034,770 | 7/1977 | Trecker .......................... | 132/321 |
| 4,550,741 | 11/1985 | Krag ............................. | 132/321 |
| 5,174,314 | 12/1992 | Charatan ......................... | 132/321 |
| 5,560,377 | 10/1996 | Donovan .......................... | 132/321 |

*Primary Examiner*—John J. Wilson
*Attorney, Agent, or Firm*—David L. Volk

[57] ABSTRACT

A plurality of lengths of floss each includes two ends and a finger loop at each of the ends. The lengths of floss are removably connected to each other to form a single, continuous piece and are stored within a dispenser. The dispenser includes an opening configured to permit the lengths of floss to be removed there-through and then separated for use.

4 Claims, 4 Drawing Sheets

5,799,673

DENTAL FLOSS WITH FINGER LOOPS AND DISPENSER

CROSS-REFERENCE TO RELATED APPLICATIONS

This application is a continuation of application Ser. No. 08/784,091, filed Jan. 15, 1997, now abandoned.

BACKGROUND OF THE INVENTION

1. Field of the Invention

The present invention relates to dental hygiene devices, specifically to dental floss with finger loops and a dispenser.

2. Description of the Related Art

Flossing is an important component of an adequate dental health regimen. To use conventional dental floss, a person usually begins by pulling a length of floss from a dispenser, and then attempts to cut the floss by urging the floss against a cutting blade attached to the dispenser. Sometimes these cutting blades don't work; as a result, the user pulls too much floss out of the dispenser at once, and some floss becomes wasted. Sometimes, so much force is applied to the floss in an attempt to cut it with the dispenser that the dispenser actually comes apart and must be re-assembled if it is to be further used.

To floss the teeth, a person usually wraps the ends of the floss around the forefinger of each hand. This can actually be painful to the fingers if the floss is wrapped too tightly, or when the floss becomes taut during use.

SUMMARY OF THE INVENTION

The tooth cleaning apparatus of the present invention includes a plurality of lengths of floss, each of the lengths of floss having two ends and a finger loop at each of the ends. The lengths of floss are removably connected to each other to form a single, continuous piece and are stored within a dispenser. The dispenser includes an opening configured to permit the lengths of floss to be removed there-through and then manually separated by twisting or pulling for use.

Accordingly, several objects and advantages of the present invention are:

a. to provide dental floss which is easily dispensed;

b. to provide dental floss which is easily used; and c. to provide dental floss which isn't painful to the fingers of a user.

Still further objects and advantages will become apparent from the ensuing description and drawings.

DETAILED DESCRIPTION

Figure 1:
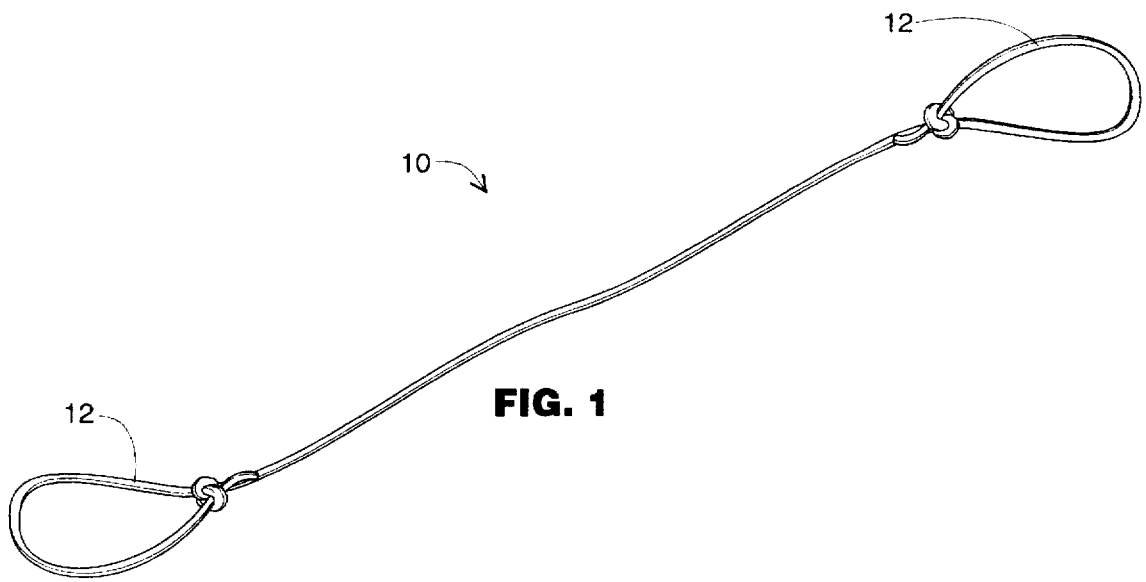
FIG. 1 is a perspective view of a length of floss, showing a finger loop at each end formed by tying.

FIG. 1 is a perspective view of a length of floss 10, showing a finger loop 12 formed at each end thereof by tying the length of floss 10 to itself. A user may insert an index finger (not shown) into each of the finger loops 12, and holding the length of floss 10 taut between his or her hands, insert the length of floss 10 between his or her teeth (not shown) to floss the teeth in a conventional manner. To improve his or her grip on the length of floss 10, the user may press his or her thumb against the index finger of the same hand, trapping a portion of the finger loop 12 between the thumb and the index finger.

Figure 2:
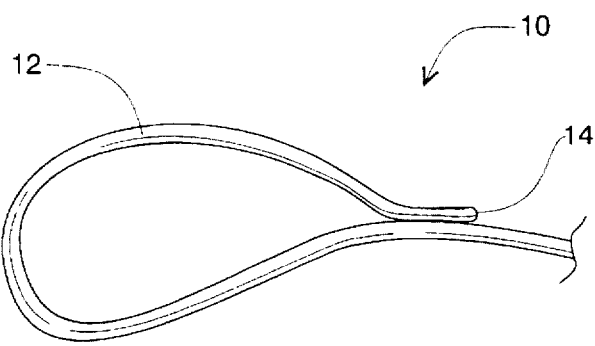
FIG. 2 is a partial perspective view of an end of the length of floss, showing an alternative embodiment of the finger loop.

FIG. 2 is a partial perspective view of one of the ends of the length of floss 10, showing an alternative embodiment of the finger loop 12. The finger loop 12 is formed by looping the length of floss 10 and adhesively bonding the length of floss 10 to itself near an extreme end 14 of the length of floss 10.

Figure 3:
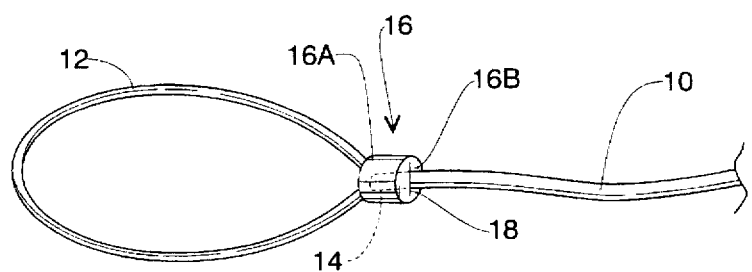
FIG. 3 is a partial perspective view of an end of the floss, showing another alternative embodiment of the finger loop.

FIG. 3 is a partial perspective view of one of the ends of the length of floss 10, showing another alternative embodiment of the finger loop 12. The finger loop 12 is formed of a polymeric material such as plastic or rubber. A collar 16 is attached to the finger loop 12.

Figure 4:
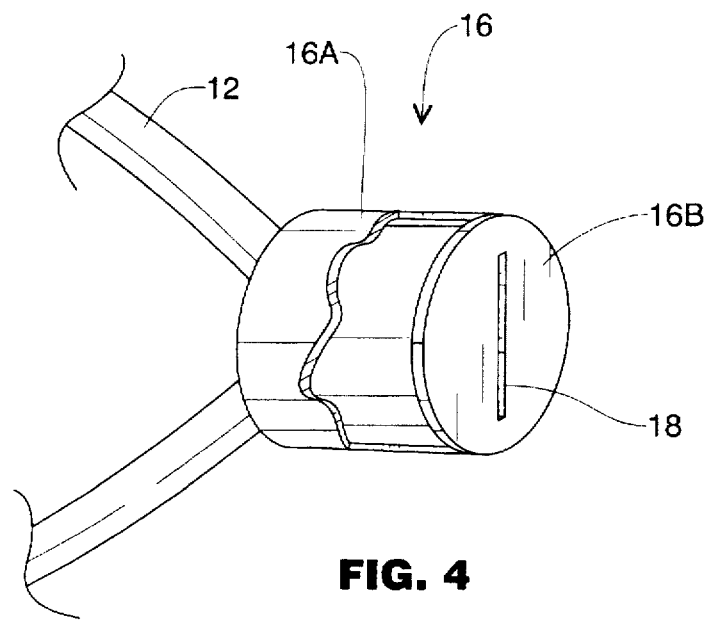
FIG. 4 is a partial perspective view of the finger loop of FIG. 3, showing the collar partially cut away.

FIG. 4 is a partial perspective view of the finger loop 12, showing the collar 16 partially cut-away, and shown without the length of floss 10, for clarity. Referring to FIGS. 3 and 4, the collar 16 includes a cylindrical wall 16A and a flat circular wall 16B disposed at a right angle to the cylindrical wall 16A. The flat circular wall 16B includes a slit 18 therein through which the extreme end 14 of the length of floss 10 is inserted.

Figure 4A:
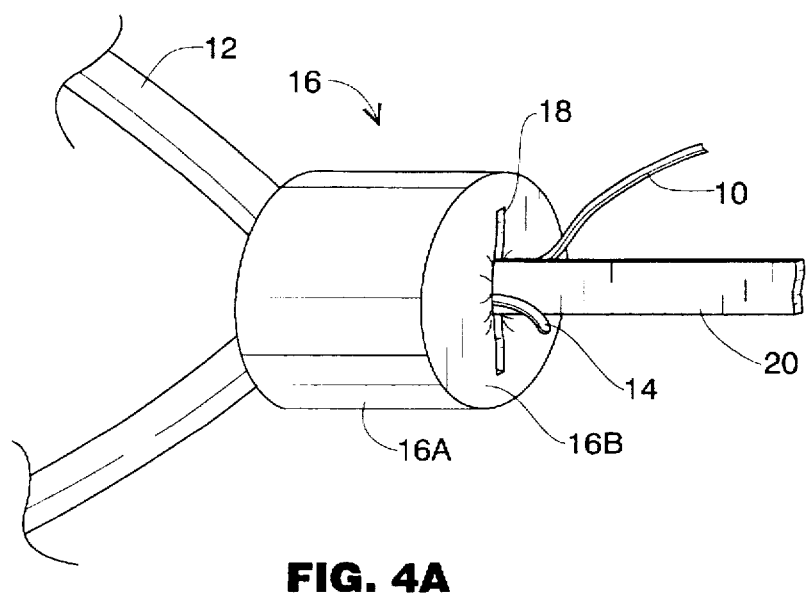
FIG. 4A is a partial perspective view of the finger loop of FIGS. 3 and 4, showing the length of floss being inserted into the collar.

FIG. 4A is a partial perspective view of the finger loop 12, showing the length of floss 10 being inserted into the collar 16 through the slit 18, using a flat, rigid elongated tool 20. The flat circular wall 1 6B is somewhat flexible, permitting the slit 18 to widen when the length of floss 10 is inserted there-through, and then to flex back to a more narrow condition after the length of floss 10 has been inserted and the tool 20 has been removed, thereby securely engaging the length of floss 10 within the slit 18. The tool 20 may be a hand tool or may be machine operated.

Although the collar 16 as shown is cylindrical, other shapes are possible, such as a rectangular, tubular shape.

Figure 5:
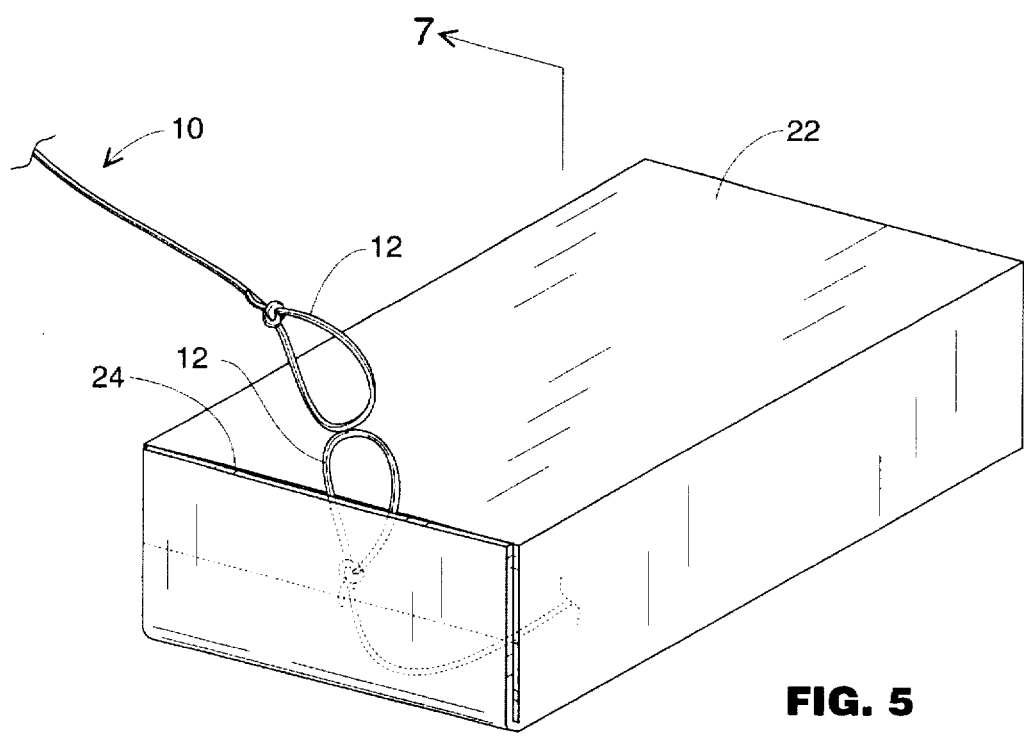
FIG. 5 is a perspective view of the lengths of floss being removed from a dispenser.

FIG. 5 is a perspective view of the lengths of floss 10 being removed from a dispenser 22. Each length of floss 10 is removably connected to an adjacent length of floss 10 to form a single, continuous piece. The lengths of floss 10 are stored within the dispenser 22 and are removable through an opening 24 within the dispenser 22.

Figure 6:
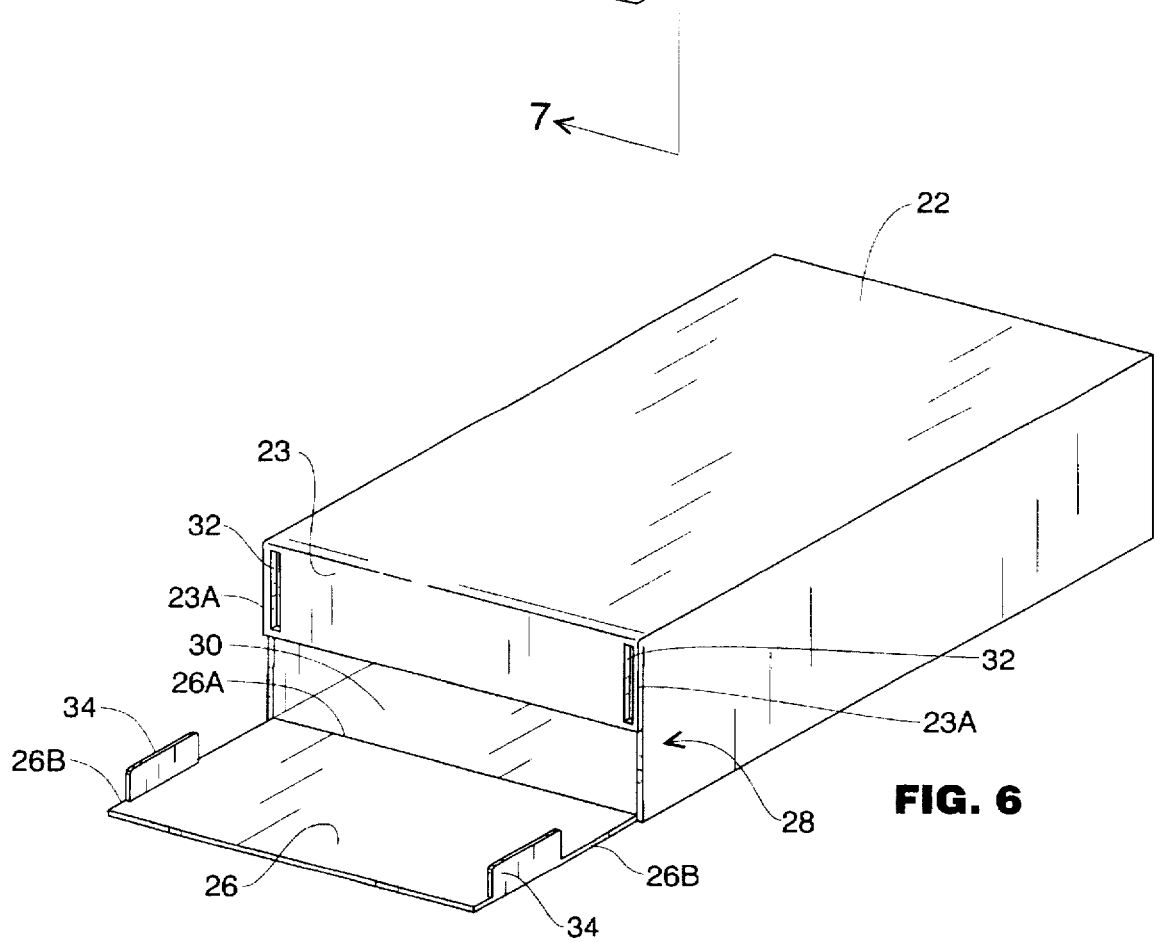
FIG. 6 is a perspective view of the dispenser.

FIG. 6 is a perspective view of the dispenser 22. The dispenser 22 is generally box-shaped, having an openable flap 26 at a first end 28 thereof. The first end 28 is partially covered by an elongated flap 23, leaving an elongated opening 30 adjacent a hinged end 26A of the openable flap 26. The elongated flap 23 includes a slot 32 disposed near each elongated flap end 23A. The openable flap 26 includes a tab 34 protruding outwardly from each openable flap end 26B at a substantially perpendicular angle to the openable flap 26. The tabs 34 are positioned to penetrate the slots 32 when the openable flap 26 is closed over the elongated flap 23 and the elongated opening 30.

Figure 7:
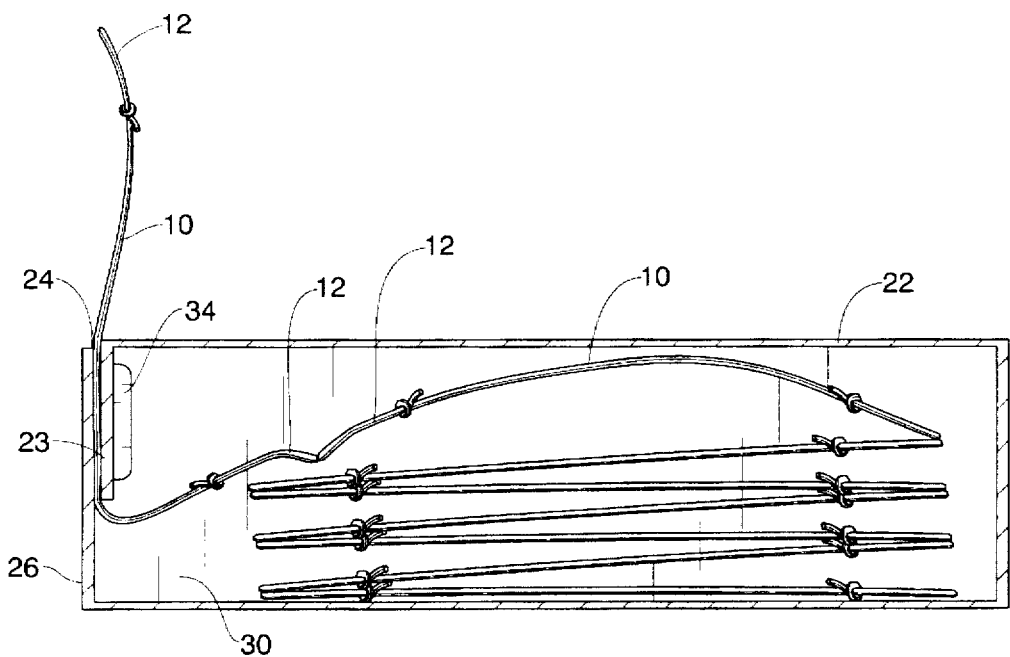
FIG. 7 is a cross-sectional view of the dispenser taken along line 7—7 of FIG. 5, showing one method of storing the lengths of floss within the dispenser.

FIG. 7 is a cross-sectional view of the dispenser 22 taken along line 7—7 of FIG. 5. In this particular embodiment, the finger loops 12 are formed by tying as shown in FIG. 1, and the lengths of floss 10 are removably connected to each other by adhesively bonding together adjacent finger loops 12. This method of removably connecting the lengths of floss 10 to each other could also be used with the embodiments shown in FIG. 2 and FIG. 3.

The lengths of floss 10 are stacked within the dispenser 22. Stacking is preferred, although other methods of storing the lengths of floss 10 within the dispenser 22 are within the scope of the present invention; for example, the lengths of floss 10 may be wrapped about a spindle (not shown). Stacking provides the advantages of simplicity and ease of manufacture and use. Sometimes with spindle type floss dispensers, the spindle itself becomes dislodged from the dispenser. Stacking as shown eliminates this problem.

The illustration of FIG. 7 shows only eight lengths of floss 10 for clarity; however, it is envisioned that many more lengths of floss 10 may be stacked or otherwise stored within the dispenser 22. Additionally, the stack is shown with the lengths of floss 10 disposed at an acute angle with respect to each other for clarity. In actual use, the lengths of floss 10 will be stacked against each other and relatively parallel to each other, except for the top one or two lengths of floss 10 when one of the lengths of floss 10 is being removed from the dispenser 22.

The lengths of floss 10 are removed from the dispenser 22 by pulling the lead length of floss 10 from outside of the dispenser 22 through the elongated opening 30, between the openable flap 26 and the elongated flap 23, and through the opening 24 formed between the openable flap 26 and the elongated flap 23.

Figure 8:
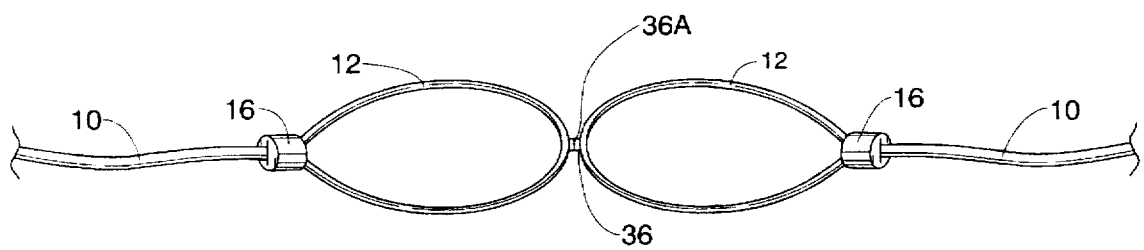
FIG. 8 is a partial perspective view of the lengths of floss, showing the finger loops of FIG. 3 connected together.

FIG. 8 is a partial perspective view of the lengths of floss 10, showing the finger loops 12 of FIG. 3 connected together. Although the lengths of floss 10 of this embodiment may be removably connected together as described with regard to FIG. 7, FIG. 8 shows an alternative method, wherein a breakable polymeric segment 36 is formed between each of the finger loops 12. The segment 36 may include a score line 36A which is somewhat weaker than the rest of the segment 36 to facilitate breaking of the segment 36 to separate the lengths of floss 10. The score line 36A may be pre-weakened by bending or by making the score line 36A of thinner polymeric material than the rest of the segment 36, by other conventional methods, or by a combination of methods. The score line 36A may be bent to facilitate stacking of the lengths of floss 10 similar to the embodiment shown in FIG. 7.

The foregoing description is included to describe embodiments of the present invention which include the preferred embodiment, and is not meant to limit the scope of the invention. From the foregoing description, many variations will be apparent to those skilled in the art that would be encompassed by the spirit and scope of the invention. The scope of the invention is to be limited only by the following claims and their legal equivalents.

The invention claimed is:

1. A tooth cleaning apparatus comprising a length of floss having two ends and a finger loop at each of the ends, wherein the finger loop is formed of polymeric material, a collar is attached to the finger loop, one of the ends of the floss is connected to the collar, the collar includes a tubular wall and a flexible wall disposed at a right angle to the tubular wall at a distal end of the collar, and the flexible wall includes a slit therein through which one of the lengths of floss is inserted.

2. A tooth cleaning apparatus comprising a length of floss having two ends and a finger loop at each of the ends, wherein the finger loop is formed of polymeric material, a collar is attached to the finger loop, one of the ends of the floss is connected to the collar, the collar includes a cylindrical wall and a flexible, flat circular wall disposed at a right angle to the cylindrical wall at a distal end of the collar, and the flat circular wall includes a slit therein through which one of the ends of the length of floss is inserted.

3. A tooth cleaning apparatus comprising a plurality of lengths of floss, each of the lengths of floss having two ends and a finger loop at each of the ends, the lengths of floss removably connected to each other to form a single, continuous piece and stored within a dispenser having an opening configured to permit the lengths of floss to be removed there-through and then separated for use, wherein the finger loop is formed of polymeric material, a collar is attached to the finger loop, one of the ends of the length of floss is connected to the collar, each of the lengths of floss is removably connected to an adjacent one of the lengths of floss by a breakable polymeric segment formed between adjacent ones of the finger loops, the collar includes a cylindrical wall and a flat circular wall disposed at a right angle to the cylindrical wall at a distal end of the collar, and the flat circular wall includes a slit therein through which one of the ends of the length of floss is inserted.

4. The tooth cleaning apparatus of claim 3, wherein the lengths of floss are connected to each other in such a manner as to form an accordion-shaped stack.

* * * * *